United States Patent [19]
Livingston

[11] 3,958,025
[45] May 18, 1976

[54] ABSCISIC ACID TABLETS AND PROCESS

[76] Inventor: Virginia W-C Livingston, 8492 Prestwick Drive, La Jolla, Calif. 92037

[22] Filed: July 5, 1974

[21] Appl. No.: 485,846

Related U.S. Application Data

[63] Continuation-in-part of Ser. No. 295,720, Oct. 6, 1972, which is a continuation-in-part of Ser. No. 82,806, Oct. 21, 1970, abandoned, which is a continuation-in-part of Ser. No. 831,982, June 10, 1969, Pat. No. 3,768,249, which is a continuation-in-part of Ser. No. 490,629, Sept. 27, 1965.

[52] U.S. Cl. .............................................. 424/317
[51] Int. Cl.² ...................................... A61K 31/19
[58] Field of Search ................................... 424/317

[56] References Cited
OTHER PUBLICATIONS
The Merck Index, 8th Ed., Merck & Co., Inc., 1968, p. 1711.

*Primary Examiner*—Stanley J. Friedman
*Attorney, Agent, or Firm*—Christen & Sabol

[57] ABSTRACT

Tablets of abscisic acid and a carrier are used to treat a vitamin deficiency of abscisic acid in man, animal and the avian species.

14 Claims, No Drawings

ABSCISIC ACID TABLETS AND PROCESS

BACKGROUND OF THE INVENTION

This is a continuation-in-part application of copending application Ser. No. 295,720, filed Oct. 6, 1972, which is a continuation-in-part of copending application Ser. No. 82,806, filed on Oct. 21, 1970, now abandoned, which is a continuation-in-part application of, and was copending with application Ser. No. 831,982, filed on June 10, 1969, now U.S. Pat. 3,768,249, which is a continuation-in-part application of, and was copending with, application Ser. No. 490,629, filed on Sept. 27, 1965.

DESCRIPTION OF THE INVENTION

This invention involves a method of treating a vitamin deficiency of abscisic acid in man, animal and the avian species. The process includes administering to the man, animal or avian species a composition comprising abscisic acid and a carrier. The abscisic acid is administered to the man, animal or avian species in an amount from 10mcq. to about 20 mg. per kg. of body weight per day. This invention also involves the composition containing the abscisic acid and carrier.

Evidence for the etiological relationship of Progenitor cryptocides to neoplastic disease has been documented over a period of years. Its cultural properties, staining characteristics, and morphology have been fully described. Its filterable bodies have been measured by electron microscope and found similar in size to some viruses. The pathology produced in experimental animals has been reported. It has also been demonstrated in fresh blood samples examined by darkfield and phase microscopy. More recently, immunological studies in guinea pigs have shown cross-reactivity with *M. tuberculosis*. In addition, the production by *P. cryptocides in vitro* of a parahormone or analogue of human chorionic gonadotropin is described. Its identification by bioimmunological and radioimmunoassay methods has been established.

SKIN REACTIONS OF GUINEA PIGS IMMUNIZED WITH CRYPTOCIDES, BCG, AND MYCOPLASMA HOMINIS TO MYCOBACTERIAL PURIFIED PROTEIN DERIVATIVES (PPD)

This was an experiment to determine how guinea pigs immunized against cryptocides, BCG, Tumor Homogenates, and Mycoplasma hominis would react to intradermal skin tests with purified protein derivatives derived from six different mycobacterial strains. Forty-two white female guinea pigs weighing from 300 – 350 grams each were distributed in groups of six into seven cages. Each group received from 0.15 to 0.2 ml. of immunizing antigen every three days. Six doses were given intreperitoneally to all but those animals receiving live BCG, which was administered only once.

PROCEDURE

The immunizing antigens were: I. Cryptocides in formalinized pooled blood cultures; II. Cryptocides in the German vaccine, from various mixed tumor homogenates; III. phenolized Mycoplasma hominis, cultured from a freshly isolated genital strain; and IV. BCG attenuated bovine tubercle bacilli, lyophilized organisms. Control animals received no immunization.

After a rest period of one week following immunization, the guinea pigs were shaved on both sides, and intradermal skin tests were performed with 25 units (0.0005 mgm per 0.1 ml.) of PPDs derived from six different strains of mycobacteria, a suspension in 0.5% phenol of 2% phenol killed cryptocides organisms. The animals were examined for any skin reactions developing within 24 to 48 hours. The results are presented in the included table.

The similar skin reactions shown by guinea pigs immunized by cryptocides strains, Mycoplasma hominis, and BCG tubercle bacilli to the various mycobacterial PPDs and cryptocides, demonstrate antigen sharing and interrelationship between cryptocides, the Mycobacteria, and Mycoplasma hominis.

The BCG immunized guines pigs gave slightly stronger reactions to the mycobacteria PPD than to the cryptocides suspension. However, this was a suspension of whole bacteria and products rather than a purified protein

| Immunizing Antigens | SKIN TEST REACTION* OF GUINEA PIGS AFTER I.P. IMMUNIZATION WITH CRYPTOCIDES, BCG, AND M. HOMINIS | | | | | | |
|---|---|---|---|---|---|---|---|
| | PPD Seibert | PPD Battey | PPD Scotochrome | PPD Fortuitis | PPD Kansasii | PPD Avian | Killed Cryptocides |
| I Cryptocides blood cultures | ++ | ++ | + | + | ± | ++ | ++ |
| II Cryptocides urine cultures | ++ | + | + | + | + | + | ++ |
| III *Suspension of formalinized pooled human tumor homogenates | ++ | + | ++ | + | + | + | ++ |
| IV Mycoplasma hominis | ± | ± | ± | ± | ± | ± | + |
| V BCG bovine Tubercle bacilli | ++ | ++ | ++ | + | + | ++ | + |
| VI Controls no. | − | − | − | − | − | − | ± |

*++ = redness and swelling
+ = redness, no swelling
± = slight redness
− = no redness, no swelling
*Vaccine produced by Albrecht & Co., Undenheim, Germany.

derivative. It is planned to produce PPD from cryptocides to be used as a standard testing material.

PROGENITOR CRYPTOCIDES AS A PRODUCER OF AN ANAHORMONE OR PARAHORMONE, CHORIONIC GONADOTROPIN IN VITRO.

The toxic fractions obtained from tumor isolates of P. cryptocides have been previously described.[39] Cultures of P. crypotcides grown in the dark at room temperature yield a dark, red-brown material when extracted with a mixture of n-butanol, glacial acetic acid and water. Reddish plates, oily residue and white crystals were observed. Similar material was obtained. A typical yield from 150 ml. urine sample gave approximately 20 mg of needlelike crystals, 5 mg. of the oil, and 10 mg of the red plates. The combined amounts appeared to represent activity of about 0.5 mg/day secreted in urine. The material at this time was not identified. However, the entire toxic endproducts were shown to increase the incidence of tumors in mice two and a half-times in the twenty week pulmonary bioassay test. Suspension of the material was demonstrated to exhibit some antibiotic properties. The white crystalline material was not separated from the red plates and oily substances at that time.

Since the mouse experiments with the entire crystalline material demonstrated an increase in the incidence of tumors that there might be a specific growth factor in the cultures of P. cryptocides. This factor is believed to be chorionic gonadotropin. With this thought in mind, cultures of P. cryptocides were grown and extracted for chorionic gonadotropin. Under certain specific cultural conditions which are readily reproducible, it was found that CGH is produced in relatively large amounts by P. crypotcides in vitro.

PREPARATION AND DEMONSTRATION OF CHORIONIC GONADOTROPIN PRODUCED BY PROGENITOR CRYPTOCIDES IN VITRO

BACTERIAL METHODOLOGY

1. Culture media

The culture media has been fluid thioglycollate medium without indicator. The dry mixed medium is purchased in 1 lb. bottles and prepared as directed so that each liter furnishes the following:

|  | Grams per liter |
| --- | --- |
| Trypticase | 17.0 |
| Phytone | 3.0 |
| Dextrose | 6.0 |
| Sodium chloride | 2.5 |
| Sodium thioglycollate | 0.5 |
| Agar | 0.7 |
| l-crystine | 0.25 |
| sodium sulfite | 0.1 |

30 grams of the dehydrated material is suspended in a liter of distilled water and heated on a Corning hot plate agitated by a magnetic stirring bar. Heating is continued for about 2 minutes after boiling. The medium is then sterilized in an autoclave at 120°C., 15 lbs. pressure for 15 minutes.

II. Organism

The organism used for innoculation of the sterile broth is a single colony from blood agar plates (phenylethyl alcohol). The organism is from patient urine isolates or blood cultures which exhibit acid-fastness. Incubation is carried out on an Incushaker at 37°C. The flasks are gently rocked. The incubation time has varied from 9 to 21 days. In all cases the growth produced good turbidity in 3 to 4 days. The time of maximum CGH production has not been established. However, little CGH is detected before the ninth day of incubation.

III. Isolation of the CGH

The entire culture media, organisms and broth are acidified to pH 4.5 – 5.0 by the addition of glacial acetic acid (75–100 ml. per 10 liters). Next 4 volumes or 40 liters of C.P. acetone are added to the 10 liter mixture producing a white precipitate.

The mixture is allowed to sit overnight at room temperature and the precipitate is recovered either by filtration or centrifugation. The final precipitate is washed with 10 ml. of dry acetone and then allowed to air dry after decanting the acetone supernatant.

This air dried fraction is always colored (tan or reddish brown). 10 mg. of this crude material dissolved in 10 ml. of distilled water is then used in the Pregnosticon test sytem. In the actual test only 0.1 ml. is used. The reaction is almost always a plus 4 reading.

Further purification of the CGH-like material can be done by resuspending the sample in distilled water. The CGH-like material is water soluble whereas the proteins and associated lipids are water insoluble. Centrifugation and/or filtration at this stage will remove the oily substances and reddish plates to yield grey-white crystals. The CGH can be reprecipitated from the water phase with 4 volumes of acetone. The oily substance and reddish plates are yet to be further characterized.

The following score system was used:

| No reaction: | less than 750 I.U./liter | 0 | 0 |
| --- | --- | --- | --- |
|  | 750–7,500 I.U./liter |  | 1 |
|  | 7,500–75,000 I.U./liter |  | 2 |
|  | 75,000–375,000 I.U./liter |  | 3 |
|  | Over 375,000 I.U./liter |  | 4 |

The results are presented in the following table.

CHORIONIC GONADOTROPIN DETERMINATIONS IN CONTROL ORGANISMS.

| NAME | VISUAL SCORE | CULTURE ORGANISM URINE | BIOASSAY |
| --- | --- | --- | --- |
| Staphylococcus Aureua | neg. |  | neg. |
| Pseudomones Acurginosa | neg. |  | neg. |
| Salmonella Typhosa | neg. |  | neg. |
| Bacillus | neg. |  | neg. |
| Klebsellia Pneumonia | neg. |  | neg. |

THE EFFECT OF CHORIONIC GONADOTROPIN FROM VARIOUS SOURCES ON MATURE FEMALE MICE

I. 5 mice Saline Control 0.25 ml/mouse per day for 10 days given I.P.

II. 5 mice 1000 i.u. of commercial human chorionic gonadotropin, 0.25 ml. I.P.

III. 5 mice 1000 i.u. of human chorionic gonadotropin, isolated from urine specimens, a composite of positives by Organon immuno-assay 0.25 ml/I.P.

IV. 5 mice 1000 i.u. of gonadotropin isolated from cryptocides cultures administered in 0.25 ml. daily.

The mice were sacrificed after weighing.

The following were determined:

Adrenal weight:
Ovary weight
Uterine weight
Any differences in body weight.

MOUSE EXPERIMENT WITH CHORIONIC GONADOTROPIN

|  | Mouse No. | 7/1/73 Wt. g. | 7/11/73 Wt. g. | Diff. Mouse | Adrenal Wt. mg. | Ovary Wt. mg. | Uterine Wt. mg. |
|---|---|---|---|---|---|---|---|
| SALINE CONTROL | 1 | 28 | 30.0 |  | 5.1 | 39 | 125 |
|  | 2 | 26 | 29.0 |  | 5.0 | 30 | 130 |
|  | 3 | 26 | 31.0 |  | 5.6 | 36 | 120 |
|  | 4 | 27 | 33.0 |  | 4.9 | 31 | 135 |
|  | 5 | 25 | 34.0 |  | 5.3 | 28 | 140 |
| Total |  | 132 | 157 |  | 25.9 | 164 | 650 |
| Av. |  | 26.4 | 32.5 | 6.1 | 5.18 | 32.8 | 130 |
| HCG COMMERCIAL PREPARATION | 6 | 29 | 21.0 |  | 4.1 | 42 | 165 |
|  | 7 | 25 | 16.0 |  | 3.2 | 46 | 170 |
|  | 8 | 26 | 20.0 |  | 3.5 | 43 | 180 |
|  | 9 | 27 | 24.0 |  | 3.7 | 44 | 182 |
|  | 10 | 28 | 25.0 |  | 4.2 | 49 | 171 |
| Total |  | 135 | 106 |  | 18.7 | 224 | 868 |
| Av. |  | 27.0 | 21.2 | −5.8 | 3.74 | 44.8 | 173.6 |
| URINE CGH | 11 | 26 | 27.0 |  | 5.1 | 34 | 130 |
|  | 12 | 26 | 24.0 |  | 3.8 | 36 | 140 |
|  | 13 | 29 | 23.0 |  | 4.9 | 37 | 145 |
|  | 14 | 31 | 24.0 |  | 4.2 | 29 | 142 |
|  | 15 | 30 | 25.0 |  | 4.1 | 31 | 141 |
| Total |  | 142 | 123 |  | 22.1 | 167 | 698 |
| Av. |  | 28.4 | 24.6 | −3.8 | 4.4 | 33.2 | 139.6 |
| ORGANISM GONADOTROPIN | 16 | 31 | 24.0 |  | 4.7 | 35 | 145 |
|  | 17 | 26 | 26.0 |  | 4.3 | 30 | 150 |
|  | 18 | 27 | 26.0 |  | 4.2 | 36 | 136 |
|  | 19 | 26 | 23.0 |  | 4.1 | 33 | 138 |
|  | 20 | 27 | 23.0 |  | 3.8 | 34 | 140 |
| Total |  | 137 | 122 |  | 21.1 | 168 | 709 |
| Av. |  | 27.4 | 24.4 | −3.0 | 4.2 | 33.6 | 142.0 |

Body weight loss was similar.

Only the commercial CGH affected the uterine weight.

Following the mouse experiments, biological testng with rats was performed as follows: Female Sprague-Dawley rats were injected intraperitoneal with the respectively materials listed below. The total volume of each injection was 0.25 ml. per day for the 4 week period. Each group was composed of 10 rats.

| Group | Material injected |
|---|---|
| I. | Saline control |
| II. | Pooled urine chorionic gonadotropin isolated from patients having a 3 or 4 plus Pregnosticon Test. The final material had a 4 plus activity and was suspended in saline. |
| III. | Bacterial chorionic gonadotropin-like material isolated from a composite of cryptocides organism (12 day culture in thioglycollate media). The final saline soluble material resulting from acetone precipitation had an activity of 2 plus using the Pregnosticon test. |
| IV. | Control chorionic gonadotropin, manufactured by Ries Biologicals, Los Angeles, California, Lot No. 73F 166 which contained 1000 USP units/cc when diluted. |

It is believed that the HCG produced by the cryptocides be neutralized by abscisic acid, an antigrowth hormone of plants. The tests demonstrate that this inhibition did occur in vitro using as little as 100 micrograms of abscisic acid per liter of culture media inoculated with crypotcides. The HCG was negative in the treated sample at the end of nine days whereas the untreated control cultures were rated 4 plus.

The abscisic acid was obtained from Calbiochem of La Jolla, Lot No. 300032 which was synthesized in pure crystalline form by Hoffman-LaRoche Inc.

The animals were weighed on day 1 and then at weekly invervals. At 28 days the animals were again weighed and sacrificed. The ovarian weights were determined at this time. Results:

Summary of weight gain and ovarian weights of rats treated with various chorionic gonadotropins and/or like materials.

|  | Initial Wt. | Final Wt. | Wt. Gain g. | Ovarian wt., mg. |
|---|---|---|---|---|
| I. Saline | 76.2 | 177.0 | 100.8 | 26.5 |
| II. Urine CGH material | 83.8 | 126.9 | 43.1 | 25.9 |
| III. Bacterial CGH material | 87.5 | 124.9 | 37.4 | 28.2 |
| IV. Control CGH | 87.2 | 143.5 | 56.3 | 40.7 |

URINE PREPARATION METHOD

Determination of chorionic gonadotropin was performed on acetone precipitate of 100 ml. aliquot of a 24-hour urine from the patient. The remainder of the test was carried out using the immuno-diagnostic pregnancy test (Pregnosticon$^R$) manufactured by Organon. The range of international units was determined by dilution of precipitate.

The bacterial or cryptocides isolate represented 1 billion organisms/cc in 25 ml. To each 25 ml. suspension, without further treatment, was added 100 ml. acetone. The precipitate was discarded. CGH determinations were carried out on the water soluble portion.

It is apparent from the above Tables that CGH produced in the urine of patients with neoplastic disease as well as the CGH-like material produced by the cryptocides organisms has a growth inhibiting or wasting effect on mice and rats. The same CGH-like material had little or no effect on increasing the ovary weights of the animals.

RADIOIMMUNOASSAY TECHNIQUE FOR ISOLATION OF CGH DERIVED FROM PROGENITOR CRYPTOCIDES

Lypohylized bacterial preparation was reconstituted with 5 ml. distilled water. 100 $\mu$l of this preparation together with a tracer of $^{125}$I Human Chorionic Gonadotropin (100,000 counts/min.) was applied to the surface of a 1 × 15 cm column of polyacrylomide molecular exclusion gel "Biogel P-4".[1] The column was eluted with 0.02 M phosphate buffer, pH 7.35, and collected in 0.5 ml, fractions. The bulk of the readioactivity was recovered in tubes 6, 7, 8, 9 and 10 (3–5 ml.). These fractions were combined, and this was assayed for CGH by radioimmunoassay, sensitive to 0.25 MIU.[2] Two other later fractions (No. 24 and No. 63) were assayed at the same time. The combined early fraction was found to contain a large amount of HCG, with a potency exceeding 10 IU per 10$\mu$l or reconstituted preparation. The other two fractions contained no HCG. Thus, the fact that the material emerged from the gel column at precisely the same fraction as authentic $^{125}$I HGC, coupled with its specific immuno-reactivity toward anti-HCG in the radioimmunoassay, strongly suggests its close identity with chorionic gonadotropin, with respect to both its molecular weight and size, and its immunological properties.

The following hormones were checked and found absent in the bacterial extract: Cortisol, testosterone, thyroid stimulating hormone (TSH), growth hormone (GH) and follicle stimulating hormone (FSH).

The antiserum made against the whole extract of cryptocides and that made against the purified fractions (HCG) from cryptocides were both positive when checked with HCG, that is, they both found HCG in an antibody - antigen reaction.

It has been demonstrated that a filter passing pleomorphic microbe, P. cryptocides appears to be etiologically involved in the production of neoplastic disease in man and animals. It has been classified as belonging to the Actinomycetales and is intermittently acid-fast. Its pathology for experimental animals has been demonstrated. It is a blood parasite in both man and animal. It can be cultured readily on appropriate media from tumors and body fluids. Recently it has been shown that it cross-reacts with a number of mycobacteria such as BCG, and Mycoplasma hominis when tested in the guinea pig. Toxic fractions from the cultures are known to increase the incidence of tumors in controlled mouse experiments. These fractions contain not only toxic antibiotic materials not characterized as yet but also crystalline material which appears to be CGH as such or as an analog or anahormone as demonstrated in experimental animal studies and by radioimmunoassay. The production of CGH by P. cryptocides in vitro may explain the occurrence of the paraendocrine syndromes found in neoplasia.

SIGNIFICANCE OF THE EXPERIMENTAL EVIDENCE THAT CHORIONIC GONADOTROPIN IS PRODUCED BY PROGENITOR CRYPTOCIDES IN VITRO

Recent evidence that human chorionic gonadotropin antiserum appears to slow down experimental tumors in mice has been presented by Y.N. Sinha, Scripps Institution in La Jolla. Breaking the chain of host dominance by the bacterial CGH may prove to have therapeutic value. The bacterial counterfeit polypeptide CGH appears to subvert from normal physiological pathways many complicated endocrine processes of the human host by action upon the pluripotential immature cell causing it to revert to its atavistic or primitive reproductive state since CGH is concerned with rapid growth of embryonic or immature tissues before differentiation and maturation occur. CGH and subsequently bacterial CGH acts as a dominant hormone having the power to direct and alter many endocrine processes either by primary synthesis or related polypeptides or by secondary stimulation of steroidgenesis. Early in the neoplastic disease, destruction of tumor cells may benefit the host as might the reduction in numbers of the invading microbial parasite but late in the disease, endocrine and metabolic processes may be irreversibly damaged by the parasitic CGH so that removal of the tumor cells and destruction of the microbes may not restore normal endocrine balance since damage to the vital hormonal, immunological, enzymatic and metabolic processes may be irreversible and irreparable. Hope for the future may lie in universal vaccination or, barring that, early recognition of impending hormonal and immunological imbalance.

The Production of HCG In Vitro by Progenitor Cryptocides. Its Neutralization by Abscissic Acid In Vitro and In Vivo.

Abscisic acid (dormin), a plant hormone occurring naturally in certain parts of plants of many varieties, is known to produce a state of dormancy in roots and seeds as well as to cause leaf abscission and ripening of fruits, has been synthesized by Hoffman La Roche. This action of A.A. in inducing dormancy of plants, roots and seeds opposes the growth promoting action of the gibberlins and auxins.

The microbe, Progenitor Cryptocides a member of the Order Actinomycetales previously described at length, produces in vitro a hormone immunologically identical to the human growth hormone, chorionic gonadotropin. However, in vivo the microbic hormone does not produce genital hyperplasia in mice and rats as does the human hormone.

Since fungi and some related microbes produce hormones similar to those of plants, it was proposed by the applicant (VWCL) that the microbic choriogonadotropin, a growth factor, might be opposed or neutralized by a growth retardant, A.A. Both the crude plant extract containing only 30% of the A.A., and the pure synthesized A.A. from Hoffman La Roche did prove to inhibit the production of microbic HCG in vitro. Progenitor cryptocides was implanted into two one liter flasks of suitable media. Into one flask 10 micrograms of A.A. was added to the culture. The other flask received no A.A. At the end of nine days, there was no microbic choriogonadotropin present by assay in the flask containing the Cryptocides and A.A. The growth of the microbes was 3+ as judged by turbidity. The control flask not inoculated with A.A. showed 4+ growth and the equivalent of 750,000,000 units of choriogonadotropin as assayed.

Following the in vitro experiments, the in vivo study of an aminal tumor model was undertaken for determination of survival rate of C57BL/6J mice with C1498 transplated tumor following treatment with abscisic acid.

The mice and the transplanted tumor stock were purchased from The Jackson Laboratory, Bar Harbor, Maine. The mice were all males. The animals were housed in polypropylene cages and were fed Purina Laboratory Chow and water ad libitum.

The tumors were excised from the stock animals and transplanted to the animals used in this experiment. Treatment was started the day following the tumor transplantation. The 1498 tumor is a myeloid leukemia. It is palpable in 3–5 days and is lethal to the host in 10–15 days.

Abscisic acid, lot No. 001022, furnished by Hoffmann-LaRoche Inc. was suspended in saline and administered as a suspension. Treatment was carried out for a total of 7 days. The following schedule was used:

| Group | Treatment | Dose per Kilo body Wt. | No. mice per Group |
|---|---|---|---|
| I. | Saline, 0.1 ml. Intraperitoneally (I.P.) | 0 | 10 |
| II. | Abscisic acid, 10 mcg. (0.1 ml.) I.P. | 1 | 10 |
| III. | Abscisic acid, 100 mcg. (0.1 ml.) I.P. | 10 | 10 |
| IV. | Abscisic acid, 100 mcg. (0.1 ml.) oral | 10 | 10 |
| V. | Abscisic acid, 1000 mcg. (0.1 ml.) oral | 100 | 10 |

Results:
At the end of 14 days. The following survivors were noted:

| Group and Treatment | No. Survivors |
|---|---|
| I. Control, saline I.P. | 3 |
| II. 1 mg./kg. abscisic acid, I.P. | 9 |
| III. 10 mg/kg. abscisic acid, I.P. | 10 |
| IV. 10 mg./kg. abscisic acid, oral | 6 |
| V. 100 mg./kg. abscisic acid, oral | 9 |

All of the remaining animals appeared to have palpable tumors.

It was concluded that abscisic acid has a marked effect in the inhibition of the C1498 tumor system in the C57Bl/6J mouse. The compound is effective by the intraperitoneal and oral route.

The presence of plant root growth inhibiting substances in human serum and urine has been demonstrated by sephladex G-10 fractionation. R. F. Scand Jr. Clinic Lab Invest., pp. 25–32, Jan 70. Thus, the serum of healthy persons can be demonstrated to have a higher inhbiting effect on plants than that of the sick or afflicted; that is, a greater amount of the inhibitory factor exists in the blood of the well person. See Analogs of abscisic Acid and/or Dormancy Hormone Structure and Activity. C. R. Academy of Science (D) Paris 270 1936–1939, 13 April 1970, Mousselon - Canet M., Mani, Durand, etc.

Radio-immuno assay studies on the rabbit serve to further evidence that the presence of abscisic acid neutralizes the tumor growth factor and thereby, in effect, is an aid to the prevention of tumors in mice.

In vitro studies conducted in a 2 liter flask containing the cryptocides produced CGH in contrast to an untreated bottle which exhibited grown microbes at a 4 plus level measurable at the end of 10 days in terms of 750,000,000 units of CGH. In a further study, 10 mcg. of abscisic acid produced no CGH and inhibited microbes growth to about 3 plus.

It was observed that abscisic acid apparently is non-toxic in the mouse even when administered I.P. in amounts of up to 10% by weight of the mouse. Thus, with a 28 gram body weight mouse, I.P. administered at 2800 mg. per week had no apparent adverse effects.

Abscisic acid and its analogs may be employed in pure form and preferably in a pharmaceutical carrier and may be administered orally or parenterally. Also impure forms of abscisic acid and its analogs such as extracts of naturally occurring sources usually of the order of 30% purity also may be administered.

Abscisic acid and its analogs are described in The Merck Index, Eighth Edition, page 1711. Synthetic methods for the production of abscisic acid and its analogs are described in U.S. Pat. Nos. 3,576,880, 3,793,375 and 3,803,217.

Abscisic acid and its analogs also may be employed in the treatment of animals and the avian species in the form of feed additives or in humans as a dietary supplement. Thus, cattle feed and chicken feed may be fortified with amounts of abscisic acid up to the above mentioned dosage. It is believed that abscisic acid or its analogs may be an essential food element and component in man, animal and avian species, much akin to the well known essential vitamins as employed in dietary supplements in man and in feed additives in animals and avian species where deficiencies are known to exist. Thus, if an abscisic acid deficiency exists, it can be treated as herein stated.

REFERENCES

1. Wuerthele-Gaspe V. ,(Livingston), and R. N. Allen. 1948. Microorganisms associated with neoplasms. N.Y. Microscopical Soc, Bull. 2: 2 – 31.

2. Wuerthele-Caspe, V. (Livingston), E. Alexander-Jackson, J. A. Anderson, J. Hillier, R. M. Allen, and L. W. Smith. 1959. Cultural properties and pathogenicity of certain microorganisms obtained from various proliferative and neoplastic diseases. Amer. J. Med. Sci. 220: 628–646.

3. Alexander-Jackson, E. 1954. A specfic type of microorganism isolated from animal and human cancer: bacteriology of the organism. Proc. VIth Int. Cong. Microbiol. Section XVII A. Rome, Italy, Sept. 1953. Growth 18: 37–51.

4. Alexander-Jacksn, E. 1966. Mycroplasma (PPLO) isolated from Rous sarcoma virus. Growth 30: 199–228.

5. Diller, I. C. 1962. Growth and morphological variability of three similar strains of intermittently acid-fast organisms isolated from mouse and human malignant tissues. Growth 26: 181–208.

6. Diller, I. C. and W. Diller. 1965. Intracellular acid-fast organisms isolated from malignant tissues. Trans, Amer. Micr, Soc. 84: 138–148.

7. Villequez, E. J. 1955. Le Parasitism Latent des Cellules du Sang chez l'Homme, en Particulier dans le Sang des Cancereux. Maloine, Paris, France.

8. Mankiewicz, E. 1965. Antigenic components shared by bacteriophages, and phase hosts: mycobacteria, Corynebacteria, and Hela Cells. Growth 29: 125–139.

9. Mazet, G. 1962. Presence d'elements alcooloacido resistants dans les moelles leucemiques et les moelles non-leucemiques. La Semaine des Hopitaux (Medicine dans le Monde). 38 e Anee, 1-2: 35.

10. Siebert, F. B., F. K. Earrelly, and C. C. Shepard. 1967. DMSO and other combatants against bacteria isolated from leukemia. Ann. N.Y. Acad. Sci. 141: 175–201.

11. Seibert, F. B., F. M. Feldman, R. L. Davis, and I. S. Richmond. 1970. Morphological, biological, and ummunological studies on isolates from tumors and leukemic bloods. Ann. N.Y. Acad. Sci. 174: art. 2, 690–728

12. Inoue, S.. M. Singer, and J. Hutchinson. 1965. Causative agent of a spontaneously originating visceral tumor of the newt Triturus. Nature 205: 408–409.

13. Pease, P. E. 1967. Tolerated infection with the sub-bacterial phase of Listeria. Nature 215: 936–938.

14. Livingston, V. Wuerthele-Caspe, and E. Alexander-Jackson, 1970. A specific type of organism cultivated from malignancy: bacteriology and proposed classification. Ann. N.Y. Acad. Sci. 174, art. 2. 636–654.

15. Alexander-Jackson, E. 1970. Ultraviolet spectrogramic microscope studies of Rous sarcoma virus cultured in cell-free medium. Ann. N.Y. Acad. Sci. 174: art. 2, 765–781.

16. Livingston, V. Wuerthele-Caspe, and E. Alexander-Jackson, 1970. A specific type of organism cultivated from malignancy: bacteriology and proposed classification. Ann. N.Y. Acad. Sci. 174, art. 2, 636–654.

17. Alexander-Jackson, E. 1954. Atypical forms of pathogenic mycobacteria. Int. Record Med. Gen. Practice Clinics 167. 7: 389–397.

18. Alexander-Jackson, E. 1945. A hitherto undemonstrated zoogleal form of Mycobacterium tuberculosis. Ann. N.Y. Acad. Sci. 46: 127–152.

19. Wuerthele-Caspe, V., (Livingston), E. Alexander-Jackson, and L. W. Smith. 1953. Some aspects of the microbiology of cancer. J. Amer. Med. Wom. Ass. 8: 7–12

20. Wuerthele-Caspe, V. (Livingston), and E. Alexander-Jackson, 1965. An experimental biologic approach to the treatment of neoplastic disease. J. Amer. Med. Wom. Ass. 20: 858–866.

21. Wuerthele-Caspe, V. (Livingston). 1953. Microbiology of Cancer. A study of a specific microorganism isolated from animal and human cancer. Its identification in tissue. The immunologic aspects both diagnostic and therapeutic. Proc. VIth Int. Cong. Microbiol. Section XVII A. Rome, Italy.

22. Leyton, A. S. and H. Leyton. 1916. Observations on the aetiology of sarcoma in the rat. Lancet i: 513.

23. Crofton, W. M. 1936. The true nature of viruses. Staples Press Ltd. London, England.

24. Nuzum, J.W. 1925. Experimental production of metastasizing carcinoma in breast of dog, and primary epithelioma in man by repeated inoculation of Micrococcus isolated from human breast cancer. Surg. Gyn. Obstet. 11: 343–352.

25. Fonti, C. J. 1958. Eziobatogenese del Cancro. Amadeo Nicola and c. Milan, Italy.

26. Clark, G. A. 1953. Successful culturing of Glover's cancer organism and development of metastasizing tumors in animals produced by cultures from human malignancy. Proc. Cong. of Microbiol. Rome, Italy.

27. Diller, I. C. 1962. Growth and morphological variability of three similar strains of intermittently acidfast organisms isolated from mouse and human malignancy tissues. Growth 26: 181–208.

28. Inoue S., M. Singer, and J. Hutchinson. 1965. Causative agent of a spontaneously originating visceral tumor of the newt Triturus. Nature 205: 408–409.

29. Seibert, F. B., F. K. Farrelly and C. C. Shepherd. 1967. DMSO and other combatants against bacteria isolated from leukemia. Ann. N.Y. Acad. Sci. 141: 175–201.

30. Gerlach, F. 1948. Krebs and Obligater Pilzparasitismus. Urban and Schwartzenberg. Vienna, Austria.

31. Scott, M. J. 1926. Clinical experiences with carcinoma antitoxin. J. Cancer 3: 1–6.

32. Glover, T. J. 1930. The bacteriology of cancer. Canada Lancet Pract. 74: 92–111.

33. Glover, T. J., M. J. Scott, J. Loudon, and M. McCormack. 1926. Study of Rous chicken sarcoma No. 1. Canada Lancet Pract. 66: 49.

34. Villequez, E. J. 1955. Le Parasitisme Latent des Cellules du Sang chez l'Homme, en particulier dans le sang de cancereux. Maloine, Paris, France.

35. Mazet, G. 1962. Presence d'elements alcooloacido resistants dans les moelles leucemiques et les moelles non-leucemiques. La Semaine des Hopitaux (Medicine dans le Monde). 38 e Annee. 1-2:35

36. Mankiewicz, E. 1965. Antigenic components shared by bacteriophages, and phage hosts: mycobacteria, corynebacteria, and Hela cells. Growth 29: 125–139.

37. Diller, I. C. and W. Diller. 1965. Intracellular acid-fast organisms isolated from malignant tissues. Trans. Amer. Micr. Soc. 84: 138–148.

38. MacPherson, I. Reversion in hamster cells transformed by Rous sarcoma virus, science 148: 1731, 1965.

39. Livingston, A. M., V. Wuerthele-Caspe Livingston, and E. Alexander-Jackson, and G. H. Wolter, 1970. Toxic Fractions obtained from tumor isolates and related clinical implications. Ann. N.Y. Acad. Sci. 174 art. 2. 675–689.

40. Beard, J. The Enzyme Treatment of Cancer, 1911. Chatto and Windus, London, England 41. Waldenstrom, J. G. 1970. Maladies of derepression, monoclonal derepression of protein forming templates. Schweiz. med. Wschr. 100, 2197–2206.

42. Gurdon, J. B. 1968, Transplanted nuclei and cell differentiation. Sci. Amer. 219: 24–35.

43. Albeaux-Fernet, M. 1973. syndromes hormonaux ectopiques. Sem. Hop. Paris, 49, no. 4. 245–256.

44. Studer, H., J. J. Staub and F. Wyss. 1971. Schweiz. med. Wschr. 101, 446–447, Nr. 13.

45. Dilman, V. M. V. N. Golubev, N. V. Krylova. 1973. Dissociation of hormonal and antigenic activity of luteinizing hormone excreted in endometrial carcinoma patients (endogenous anahormones) Am. J. Obstet. Gynecol. 115, no. 7. 966–971.

46. Livingston, Wuerthele-Caspe, V., A. M. Livingston. 1972. Demonstration of Progenitor Crypotcides in the blood of patients with Collagen and neoplastic diseases. Transactions of N.Y. Acad. Sci. Series II, Vol. 34, No. 5. 433–453

47. Cantow, M. J. R. and J. E. Johnson. 1967. J. Appl. Pol. Sci. II, 1851.

48. Midgley, A. R. Jr. 1966. Endocrinology. Vol. 79, 10.

What is claimed is:

1. The method of treating a vitamin deficiency of abscisic acid in man, animal or the avian species, which comprises administering to said man, animal or avian species a composition comprising abscisic acid and a pharmaceutical carrier or food supplement or feed additive, said abscisic acid being administered to said man, animal or avian species in an amount from 10 mcg. to about 20 mg. per kg. of body weight per day.

2. The method as described in claim 1 wherein the administration to said man, animal or avian species, is oral or parenteral.

3. The method of claim 1 wherein said composition is in the form of a tablet.

4. The method of claim 1 wherein said pharmaceutical carrier is starch and flavoring.

5. The method of claim 1 wherein said pharmaceutical carrier is a saline solution.

6. The process as described in claim 1 wherein said composition comprises a feed additive and abscisic acid.

7. The process as described in claim 1 wherein said composition comprises a pharmaceutical carrier and abscisic acid.

8. The process as described in claim 1 wherein said composition comprises a dietary supplement and abscisic acid.

9. The process as described in claim 1 wherein said abscisic acid is administered to said man, animal or avian species in an amount of about 10 mg per kg. of body weight per day.

10. The process as described in claim 1 wherein said abscisic acid is administered to said man, animal or avian species in an amount of about 10 mg per kg. of body weight per day.

11. A composition in tablet form for the treatment of a vitamin deficiency of abscisic acid in man, animal or the avian species which comprises abscisic acid, in an amount ranging from about 10 mcg. to 20 mg. per kg. of body weight per day, in admixture with a carrier.

12. The composition of claim 11 wherein said carrier is starch and flavoring.

13. The composition of claim 11 wherein said carrier is a feed additive base.

14. The composition of claim 11 wherein said carrier is a food supplement.

* * * * *

UNITED STATES PATENT OFFICE
CERTIFICATE OF CORRECTION

Patent No. 3,958,025            Dated May 18, 1976

Inventor(s) Virginia W-C Livingston

It is certified that error appears in the above-identified patent and that said Letters Patent are hereby corrected as shown below:

In the patent heading, item [63], Related U.S. Application Data, line 4, cancel "831,982" and insert therefor --831,985--.

In the patent heading item [63], Related U.S. Application Data, line 5, cancel "Pat. No. 3,768,249" and insert therefor --abandoned--.

In the patent heading, item [63], Related U.S. Application Data, line 7, between "1965" and the period, insert --,abandoned--.

*Signed and Sealed this*

*Eleventh* Day of *October 1977*

[SEAL]

Attest:

RUTH C. MASON        LUTRELLE F. PARKER
*Attesting Officer*        *Acting Commissioner of Patents and Trademarks*